US005869645A

United States Patent [19]
Groves

[11] Patent Number: 5,869,645
[45] Date of Patent: Feb. 9, 1999

[54] METHOD FOR ISOLATING HIGH MOLECULAR WEIGHT ANTINEOPLASTIC GLYCANS USING UREA

[75] Inventor: Michael Groves, Deerfield, Ill.

[73] Assignee: Board of Trustees of the University of Illinois, Urbana, Ill.

[21] Appl. No.: 950,654

[22] Filed: Oct. 15, 1997

[51] Int. Cl.$^6$ .............................. C07H 1/06; C07H 1/00; A61K 45/00
[52] U.S. Cl. ................... 536/124; 536/123.1; 424/282.1
[58] Field of Search ................................ 536/124, 123.1; 424/282.1

[56] References Cited

U.S. PATENT DOCUMENTS

| | | | |
|---|---|---|---|
| 4,307,229 | 12/1981 | Liav et al. | 536/120 |
| 4,394,502 | 7/1983 | Maruyama | 536/119 |
| 4,843,067 | 6/1989 | Liu | 536/123 |

FOREIGN PATENT DOCUMENTS

| | | |
|---|---|---|
| 0 450 792 A2 | 10/1991 | European Pat. Off. . |
| 0 459 367 A1 | 12/1991 | European Pat. Off. . |
| WO 91/12019 | 8/1991 | WIPO . |

OTHER PUBLICATIONS

Wang et al., *Biochem. J*, vol. 311, pp. 867–872, An Antineoplastic glycan from *Mycobacerium bovis* (BCG vaccine) (1995).

Lou et al., *J. Pharm. Pharmacol*, vol. 46, pp. 863–866, In–vivo and in–vitro targeting of a murine sacrcoma by gelation microparticles loaded with glycan (PS1) (1994).

Lou et al., *Anticancer Res.*, vol. 14, pp. 1469–1475, Initial characterization of an antineoplastic, polysaccharide–rich extract of *Mycobacterium bovis* BCG, Tice substrain (1994).

Saini et al., *Phytochemistry*, vol. 20, pp. 641–645, Alpha--glucan synthesis in the cotyledons of germinating lupins (1981).

Pagano et. al., *Starch/Starke*, vol. 45, pp. 203–205, Endosperm alphal, 4–alphal,6 glucopolysaccharides. Utilization during germination of sweet corn and other maize genotypes (1993).

Mahavi Sekharam et. al., *Food Chemistry*, vol. 31, pp. 85–91, Structural studies of a glucan isolated from blue--green alga *Spirulina platensis* (1989).

Coogan et al., *Carbohydrate Res.*, vol. 218, pp. 201–209, Structural studies of aminoglucan and a soluble glucan produced from starch by *Streptococcus sanguis* 1 MC 204 (1991).

Donmez et al., *Anticancer Research*, vol. 17, pp. 445–450, Activity of a Mycobacterial Antineoplastic Glycan against Human Breast Cancer (1997).

Whistler et al.,*Adv. Carbohydr. Chem. Biochem*, vol. 32, pp. 235–275, Noncytoxic, Antitumor polysaccharides, (1976).

Database WPI, Section Ch, Week 9416, Derwent Publications, Ltd., London, GB; (1994) JP–6080574 A 940322, Abstract Only.

*Primary Examiner*—Marian C. Knode
*Assistant Examiner*—Everett White
*Attorney, Agent, or Firm*—McDonnell Boehnen Hulbert & Berghoff

[57] ABSTRACT

A method for preparing a highly potent glycan extract from Mycobacteria by admixing at least one Mycobacterium with an aqueous solution of concentrated urea.

12 Claims, 2 Drawing Sheets

METHOD FOR ISOLATING HIGH MOLECULAR WEIGHT ANTINEOPLASTIC GLYCANS USING UREA

BACKGROUND OF THE INVENTION (1) Field of the Invention

This invention concerns a method for preparing a highly purified glycan extract, as well as the purified glycan product.

(2) Description of the Art

Bacillus Calmette Guérine (BCG) vaccine is an attenuated form of *Mycobacterium bovis* that has been used as tuberculosis vaccine for more than 70 years. BCG has proved to be a general immunostimulant and intravesicular BCG immunotherapy is currently an approved and effective clinical intervention against superficial bladder cancer, providing long-term protection from tumour recurrence, progression and mortality. BCG has also been demonstrated to be effective against other tumours such as melanoma, sarcoma, lung cancer and leukemia. Success in the treatment of these tumours with BCG has proved to be variable since direct contact between BCG and the tumour cells is apparently required.

The mode of action of BCG against bladder carcinoma is not well understood, but activity has been attributed to a nonspecific stimulation of the lymphoreticuloendothelial system. BCG vaccine consists of a mixture of dead and living whole organisms with associated cell debris and approximately 5% of cancer patients treated with BCG experience adverse reactions to the therapy associated with the use of viable bacteria. These reactions include mild fever, urethritis and, in extreme situations, disseminated mycobacterioses. Thus, it is preferable to identify and isolate non-viable bacterial components of BCG with anticancer activity which could provide material with potential clinical application.

Hardham & James (1980) reported the presence of a covering material on the surface of the Glaxo substrain of BCG vaccine. This observation was shown to be more general for other BCG substrains and accounted for the lack of effect of wetting agents on the state of dispersion. The composition of the interfacial integument appears to be substantially polysaccharidic although cell-surface proteins account for the major part of cellular surface charges. Rastogi et al., (1986) found polysaccharide-rich outer layers in 18 mycobacterial species but Kristensen et al. (1992) showed that the cationic charge of BCG could be abolished with proteolytic enzymes, suggesting that it was essentially due to surface protein. The anionic charge, on the other hand, was provided by carboxylic acids, phosphoesters and strong acidic groups such as sulfate. Accordingly, it was of interest to note that the cellular integument could be removed with bacterial pronase, apparently without killing the cells. Electron microscopy and light microscopy demonstrated that aggregates of BCG cells were often covered by variable amounts of the integument. A more detailed study suggested that the integument separated by pronase was substantially carbohydrate in composition. The integument was patchy in appearance and of variable thickness, leading to the suggestion that growth of integument may be provoked by environmental stresses such as oxygen tension. Klegerman et al. (1996) recently reported that the electron transparent zone associated with the integument varied in thickness from 1–250 nm and suggested that it may be the source of complex glycans extracted from BCG from boiling water. These glycans, accounting for as much as 12% of the dry cell weight of the Tice® BCG substrain, were shown to possess considerable antineoplastic activity. Of the mixed glycans separated by boiling water extraction from the Tice® substrain of BCG vaccine, one glucan, PS1 A1, was shown to have the highest specific activity against a murine sarcoma model in vivo but no in vitro activity was detected against a wide variety of tumour models, indicating an immunostimulant mechanism (Wang et al., 1995).

Various methods have been developed for obtaining extracts of glycans and other popolysaccharides from various sources such as bacteria, yeast and plants. Furthermore, it has previously been demonstrated that complex high molecular weight antineoplastic glycans can be extracted by boiling intact cells of Mycobacteria, especially *M. bovis* (BCG vaccine), *M. vaccae* and *M. phlei*. Despite these advances in processes for obtaining therapeutic glycans from various natural sources, there remains a need for processes capable of producing glycan extracts in high purities and yields.

SUMMARY OF THE INVENTION

It is an object of this invention to provide a method for enhancing the yield of glycans and other polysaccharides extracted from cells of all types.

It is another object of this invention to provide a glycan extract of Mycobacteria.

In one embodiment, this invention is a method for extracting glycans from Mycobacteria. The method includes admixing at least one Mycobacterium strain with an aqueous urea solution for a period of time sufficient to give a glycan extract.

In another embodiment, this invention is a method for preparing a glycan extract of Mycobacterium. The method is accomplished by admixing at least one Mycobacterium selected from the group consisting of *M. bovis, M. phlei,* or *M. vaccae* and mixtures thereof with at least one protease in an aqueous solution. The combination is admixed for a period of time ranging from about 30 minutes to about 6 hours and at a temperature ranging from about 4° C. to about 40° C. to give a protease treated Mycobacterium including detached integument. The detached integument is then separated from the cells and associated cellular debris using a Ficoll-Histopaque density gradient. The detached integument is next admixed with an aqueous urea solution having a urea concentration of from about 1M to about 9M for a period of time ranging from about 1 hour to about 3 days or more at about room temperature to give a urea-extracted glycan. The glycan extract is finally recovered from the urea admixture.

DESCRIPTION OF THE CURRENT EMBODIMENT

Figure 1:
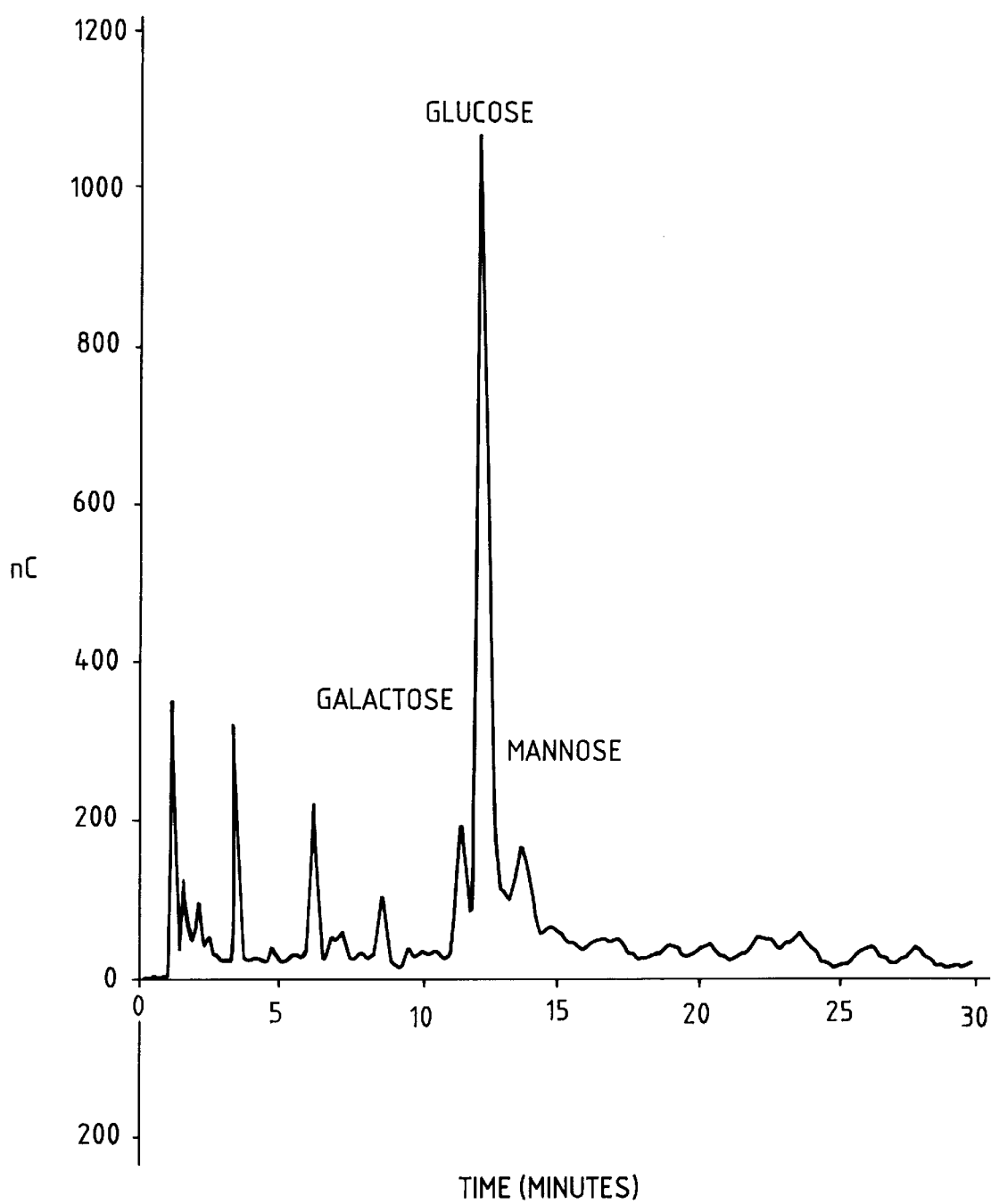
FIG. 1 is an HPLC profile of the Connaught BCG integument boiled extract prepared by hydrolyzing with TFA for one hour, air dried and redissolved in distilled water. The solution was then passed through a Dionex DX 500 Chromatographic System with an ED-40 eletrochemical detector and the data analyzed using Peaknet™ software. The peak analysis indicated that the extract included 76.0 wt % glucose, 11.42 wt % galactose, and 12.57 wt % mannose.

The present invention relates to a method for preparing a glycan from one or more Mycobacteria using a solution of cold, high concentration urea. Glycans are complex high molecular weight polysaccharides obtained from a number of natural sources including, but not limited to, fungi, bacteria and Mycobacteria. Considered to be cell wall components, these materials often have immunomodulatory activity and some have marked antineoplastic activity. Mycobacterial antineoplastic glycans (MAG's) were identified in boiling water extracts of the virulent Aoyama B substrain of *M. tuberculosis*. In addition, MAGs are present in avirulent mycobacteria such as *M. bovis* (BCG vaccine) *M. vaccae* and *M. phlei*.

The glycans of *M. bovis* are associated with the extracellular integument which is readily removed by digestion with nonspecific proteases. Once separated from the stripped cells by centrifugation in a Ficoll gradient the integument may be solubilized. One method for solubilizing the integument is by boiling in water. This method is described in U.S. patent application Ser. No. 08/540,002 which is incorporated herein by reference. An even more effective method to isolate and purify glycans from cell integument is to digest the integument in an aqueous urea solution. The glycan extraction is preformed at a high urea concentration of from about 1M to about 9M or more. It is preferred that the extraction occurs using an aqueous solution of from about 7.5M to about 8.5M urea.

The integument should be digested in the urea solution for a period of time sufficient to extract glycans from the integument. It is preferred that the integument is digested in the aqueous urea solution for a period of time ranging from about 30 minutes to about 5 days or more with an extraction time of from 8 hours to about 72 hours being preferred.

The temperature of the aqueous urea solution must be sufficient to extract glycans from the integument without destroying the glycans. The extraction may occur at temperatures of from about 4° C. to about 40° C. or higher with extraction at room temperature being preferred.

Prior to urea extraction, the mycobacterium may be treated with proteases in order to detach the integument coating the Mycobacterium cell wall. Generally proteases are necessary to detach the integument from mycobacterium that has a thick integument such as *M. bovis* and *M. phlei. M. vaccae,* on the other hand, does not need to be treated with protease prior to urea extraction. The protease treatment step, if used, is performed with, for example, streptomyces protein type XIV protease (Sigma) at a concentration of from about 1.0 to about 10.0 units/mL in sealed aseptically filled tubes at room temperature for 10 minutes to about 6 hours or more.

Biological activity of glycans obtained by digestion of Mycobacterium integument in an 8M urea solution was retained against a murine S180 sarcoma model although the specific activity of the urea extract was considerably higher than that obtained by boiling on a weight-in-weight basis. In general, the apparent molecular weight of fractions obtained by urea extraction is higher. Glycans extracted from Mycobacterium integument with urea are preferably dialysed and lyophilized to give a solid glycan extract. The preferred solid glycan extract should have an S180 mouse sarcoma cell specific activity of at least 50,000 units/mg.

Glycans can be extracted from *M. vaccae* using cold urea without protease pre-treatment. The Mycobaceterium extracted glycan appears to be a mixed glycan containing rhamnose, mannose and arabinose covalently bonded to a peptide fragment and a unstable glycan (containing only glucose). *M. vaccae* has only a thin extracellular integument which is not readily separated by non-specific protease. In the case of the *M. vaccae* extracts, the main difference between boiling water glycan extract and the urea extracts respectively is the fact that the glucosidic fraction appears to be larger in the urea extract. This suggests that both processes are affecting hydrogen bonding, with hydrolytic breakdown of the labile glucose occurring on boiling. Thus, the urea may induce conformation changes but these are restored in solution when the urea is removed by dialysis.

Sephadex G-75 column chromatography of the dialyzed urea extracts (PS4A) showed four main components (PS4A 1-4) and one, PS4A3, was resolved into three subsets by Bio-Gel PIO (PS4A 3-1 through 3). Gel filtration HPLC enabled the various fractions to be characterized and identified. PS4A3 accounted for 90% of the total extract weight with 37% protein and 25% sugar. PS4A3-1 and PS4A3-2 contained much of the protein component whereas PS4A3-3 accounted for 73% of the sugars, mainly glucose and mannose. However, none of the PS4A3 fractions had any significant biological activity against an in vivo murine S180 sarcoma model. On the other hand, both hot water extracted PS4A-1 and urea extracted PS4α-1 had activities between 0.1 and 1.0 μg/mouse (<40 μg/kg), similar to the activity of the crude extracts, although these fractions accounted for less than 10% of the total extract weight.

Antibodies against PS4 were raised in rabbits and used to identify components by SDS/PAGE and Western blot techniques. No cross-reactivity was observed against BCG components or a nonspecific anti-BCG serum. A band at the 20 kDa level was shown to be a consistent component of PS4A or PS4α. The protein was isolated and partially sequenced, having 70% homology with a published sequence for an cationic transport ATP-ase found in *M. tuberculosis.*

Pronase digestion of PS4A gave glucose and a 4 kDa component identified by NMR as a poly (1,3 α mannan). The molecular weight of the PS4α material, prepared in the cold by urea dissociation, was higher, with a higher proportion of glucose monomer. Pronase digests also had no in vivo biological activity.

The intact PS4α-1 molecule is envisaged as consisting essentially of the core 20 kDa protein to which is attached a stable poly(mannan) and a labile poly(glucan). The overall molecular weight of this highly active material is approximately 750 kDa although self-aggregation is evident in aqueous solution since particles up to 500 nm diameter could be detected by photoncorrelation spectroscopy.

EXAMPLE 1

This Example describes the preparation of a purified glycan extract from lyophilized Connaught Mycobacterium BCG.

Commercially available lyophilized BCG vaccine, lot #739-11 (obtained as a courtesy from Connaught Laboratories, Toronto, Ontario, Canada) was reconstituted with sterile water and inoculated into flasks containing 125 mL freshly prepared Middlebrook 7H-9 medium (Chadwick, 1982). The flasks were manually shaken twice a day to allow the bacteria to grow as a sedimented pellicle. The flasks were incubated for five weeks at 37° C. before harvesting.

A. Enzymatic treatment

BCG was collected from the flasks and concentrated by centrifugation for 10 minutes at 6000 rpm in sterile mL Fisherbrand® conical tubes (Fisher Scientific, Pittsburgh, Pa.). Protease type XIV (pronase) from *Streptomyces griseus* (Sigma Chemical Company, St. Louis, Mo.), dissolved in sterile phosphate buffered saline (PBS, sodium chloride (8.0 g/liter), potassium chloride (0.2 g/liter), sodium phosphate dibasic (1.15 g/liter) and potassium phosphate monobasic (0.12 g/liter)), was added aseptically through a sterile 0.2 μm low protein binding syringe filter (Gelman Sciences, Ann Arbor, Mich.), to the BCG dispersion at a concentration of 1 mg pronase/mL BCG dispersion (Devadoss et al., 1991 b; Klegerman & Groves, 1992). The tubes were sealed and placed in a Hematology/Chemistry mixer (Fisher) at room temperature for 60 minutes. The resulting enzyme treated BCG included stripped cells and detached integument.

B. Integument separation

The detached integument and stripped cells had different densities and were separated centrifugally. Sterile Histopaque®-1077 (Sigma), a Ficoll-Histopaque preparation, was added (5.0 mL) to each of eight 15 mL Fisherbrand™ culture tubes (Fisher); 3 mL of the dispersion containing BCG was layered over the Histopaque. The tubes were then centrifuged at 2000 rpm in a swinging bucket rotor for 7 minutes. Samples were collected from the middle of the supernatant and from the bottom of the tube for scanning electron microscope (SEM) examination. The remainder of the supernate was aspirated with a sterile pipette and placed in a sterile centrifuge tube. Both the supernate and pellet were washed twice with sterile deionized and distilled water to remove residual Histopaque and protease. The supernated layer containing the integument and pellet (stripped cells) were frozen and lyophilized in a Lyph-Loc® 4.5 L freeze-dryer (Labconco®, Kansas City, Mo.) prior to further examination.

C. Preparation of integument extract

1. Heat

Approximately 276 mg of the collected integument fraction was extracted in a boiling water flask by refluxing with distilled water (500 mL) for 2 hours. The solution was passed through a 0.22 μm pore size membrane filter (Millipore Corp., Bedford, Mass.) and concentrated by vacuum rotary evaporation to approximately 5–10 mL using a Büchi Rotavapor® RE111 (Büchi, Switzerland) at 60°–65° C. The concentrated water extract was dialyzed overnight through Spectra/Por 2 tubing with a molecular weight cut off of 12–14 kDa (Spectrum Med. Ind., Los Angeles, Calif.), against 2 liters of distilled water and stored in a refrigerator (Lou et al., 1994). The crude extract remained within the tubing and was lyophilized for storage and evaluation. Quantitation was gravimetric.

2. Urea

Lyophilized integument preparations were added to aqueous 8M urea and stirred at ambient room temperature for 24 hours. The samples were then filtered, concentrated and dialyzed against distilled water as above to give a purified integument extract.

Extraction of the insoluble integument with boiling water, followed by dialysis through a 12–14 MWCO membrane to remove lower molecular weight components provided a yield of 9.6% w/w dialyzed glycan. However, the yield increased to 58.3% w/w when the cold urea digestion process was used instead. Measurements of the molecular weights of the two extracts suggested that the molecular weight of the urea-processed material was approximately the same as that of the boiled material, 100–110 kDa cf 115–180 kDa.

EXAMPLE 2

The glycan extracts prepared in Example 1 were assayed. The S180 II murine sarcoma assay method is described by Klegerman et al. (1991). Briefly, S180 II murine sacrcoma cells (obtained from the American Type Culture Collection, Rockville, Md.) were maintained in vitro in Eagle's Minimal Essential Medium (Gibco, Gaithersburg, Md.) together with non-essential amino acids, Earle's basal salts, 5% calf serum, penicillin 100 units/mL and streptomycin 100 μg/mL in an atmosphere of 5% $CO_2$-95% air at 37° C.

Eight week old female Swiss-Webster CFW mice (n=10, per dose) were inoculated subcutaneously in the right flank with $3 \times 10^5$ viable S180 cells mixed with the material to be tested. Fourteen days later, the mice were sacrificed, dissected and scored for tumour incidence relative to a control group receiving tumour cells plus PBS. The linearity of the dose-response curve had been established earlier by Klegerman et al. (1991). One unit of inhibitory activity was defined as the minimum quantity of active principle sufficient to cause a significant (Fisher's exact test) decrease in the tumour incidence relative to controls, determined by assay of at least three dilutions of each fraction and extrapolated to the point of significance.

Biological activity

Activity data, Table 1, showed that the original encapsulated cellular suspension had a lower activity than that of the equivalent cells stripped. The activity of the unfractionated but pronase-treated cells suspension was higher than the untreated cells, suggesting that increased exposure of the integument surfaces may be influencing activity. The stripped cells themselves had some activity, most probably because they are still viable, are better dispersed and possibly continued to secrete integumental materials during the test period.

TABLE 1

Biological activity of Connaught BCG fractions before and after pronase digestion and separation of integument

| Fraction | Specific Activity (units/mg dry wt) |
| --- | --- |
| Connaught BCG | 5.6 |
| Pronase-treated BCG (not separated) | 12.5 |
| Separated intact integument | 50 |
| BCG stripped and viable cells (pellet) | 67 |
| Integument extract, boiling | 6,250 |
| Integument extract, urea | 55,600 |

The major differences in potency were seen between the solubilized integument extracts prepared by the boiling and urea extraction methods. Compared to the insoluble but separated integument the boiled extract was 125 times more active on a weight basis and the urea extract had 1,100 times the original activity.

Figure 2:
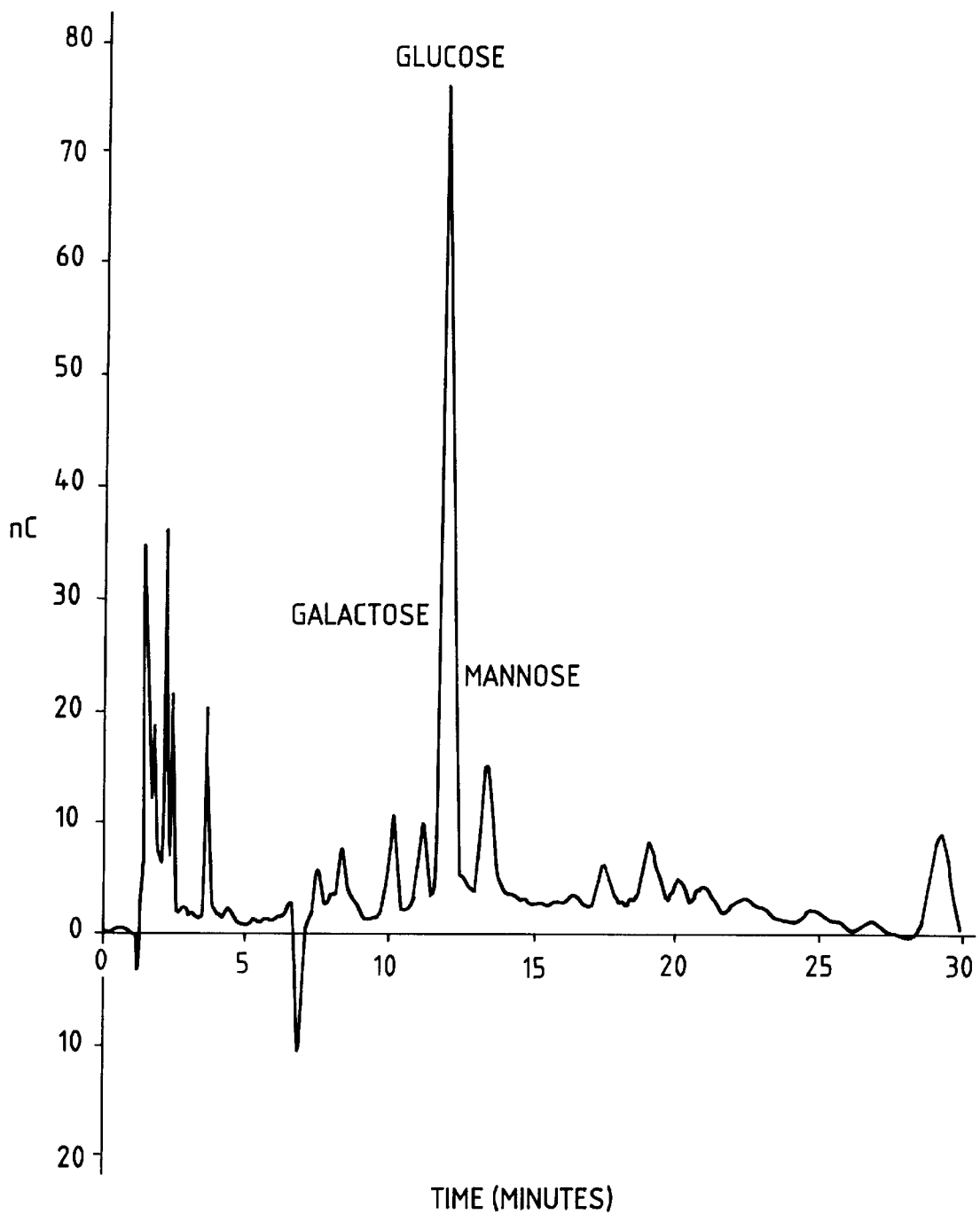
FIG. 2 is an otherwise identical HPLC profile of the Connaught BCG integument that was extracted with a cold urea solution and analyzed. The peak analysis indicated that the extract included 69 wt % glucose, 12.0 wt % galactose, and 19.0 wt % mannose.

The chromatographic profiles of the two extracts were similar as shown in FIGS. 1 and 2.

EXAMPLE 3

This Example details a method for preparing an integument extract of *M. vaccae*.

*Mycobacterium vaccae* (ATCC #15483, batch #88 09) was purchased from the American Type Culture Collection (Rockville, Md.) and cultivated in tryptic soy broth (Gibco Laboratories, Grand Island, N.J.) at 37° C. for 5–7 days. Bacterial cells were collected by centrifugation at 10,000 rpm for 20 minutes using a Sorval IZC 5B refrigerated superspeed centrifuge (DuPont Instruments, Newtown, Conn.) and washed twice with double distilled water. Washed cells were lyophilized using a Labconco Lyphlock® 4.5 Freeze Drying System (Labconco, Kansas City, Mo.). All other reagents and materials were purchased from Fisher Scientific (Fairlawn, N.J.), Sigma Chemical Company (St. Louis, Mo.) or as noted.

Extraction of immunostimulants

1. Heat: Approximately 0.5 g of lyopolized cells was suspended in 500 mL double distilled water and boiled under reflux for two hours. When cool, the suspension was passed through a 0.2 μm membrane filter and concentrated to a volume of 12–14 mL under low pressure at 65° C. using a Büchi Rotovapor® (Brinkman Instruments, Westbury, N.Y.). The concentrate was dialyzed against 2 L, distilled water overnight using a 3.5 kDa molecular weight cut-off dialysis membrane before lyophilization to give a crude extract.

2. Approximately 0.5 g of the lyophilized cells were added to 200 mL of 8M urea and stirred for about 72 hours at ambient room temperature to give a urea extract. The urea extract was filtered through a 0.2 μm membrane, and dialyzed through a 3.5 kDa MWCO membrane. The filtrate was concentrated and lyophilizing as with the crude extract and the purified extract was collected. The integument on *M. vaccae* is thin and attempts to remove it with pronase proved inconclusive. However, intact cells of seven day cultures of *M. vaccae* (ATCC No. 15483), grown on tryptic soy broth, could be extracted with boiling water or 8M urea. After filtration, dialysis (MWCO 3.5 kDa) and lyophilization, the resulting glycans appeared to be substantially similar in composition although yields by urea extraction in the cold were higher, 10–18% vs 5.6% with hot water extraction.

What I claim is:

1. A method for extracting glycans from Mycobacteria comprising admixing at least one Mycobacterium strain with an aqueous urea solution for a period of time sufficient to give a glycan extract.

2. The method of claim 1 wherein the Mycobacteria is selected from a strain selected from the group consisting of *M. bovis, M. vaccae,* and *M. phlei.*

3. The method of claim 1 wherein the Mycobacterium is admixed with an aqueous urea solution having a concentration of from about 1M to about 9M or more.

4. The method of claim 1 wherein the aqueous urea solution has a temperature ranging from about 4° C. to about 40° C.

5. The method of claim 1 wherein the Mycobacterium is admixed with the aqueous urea solution for a period of time ranging from about 1 hour to about 4 days or more.

6. The method of claim 1 wherein the Mycobacteria is admixed with at least one protease for a period of time sufficient to detach at least a portion of an integument coating the Mycobacteria.

7. The method of claim 6 wherein the protease is from *Streptomycen griseus.*

8. The method of claim 1 wherein the glycan extract is filtered, dialysed, and then lyophilized to give a solid glycan extract.

9. A method for preparing a glycan extract of Mycobacterium comprising the steps of:
   (a) admixing at least one Mycobacterium selected from the group consisting of *M. bovis, M. phlei,* or *M. vaccae* and mixtures thereof with at least one protease in an aqueous solution for a period of time ranging from about 30 minutes to about 6 hours at a temperature ranging from about 4° C. to about 40° C. to give a protease treated Mycobacterium including detached integument;
   (b) admixing the detached integument with an aqueous urea solution having a urea concentration of from about 1M to about 9M for a period of time ranging from about 1 hour to about 3 days or more at about room temperature to give a urea extracted glycan; and
   (c) recovering the glycan extract from the urea admixture of step (b).

10. The method of claim 9 wherein the detached integument is separated from the admixure of step (a).

11. The method of claim 10 wherein the separation is achieved by centrifugation.

12. The method of claim 9 wherein the glycan extract is filtered, dialysed, and then lyophilized to give a solid glycan extract.

* * * * *